United States Patent [19]

Haas et al.

[11] 4,235,976
[45] Nov. 25, 1980

[54] USE OF PHOSPHONATES AS TRIMERIZATION CATALYSTS FOR THE PRODUCTION OF POLYISOCYANURATE SYNTHETIC RESINS

[75] Inventors: Peter Haas, Haan; Rolf Wiedermann, Bergisch-Gladbach, both of Fed. Rep. of Germany

[73] Assignee: Bayer Aktiengesellschaft, Leverkusen, Fed. Rep. of Germany

[21] Appl. No.: 52,524

[22] Filed: Jun. 27, 1979

[30] Foreign Application Priority Data

Jul. 14, 1978 [DE] Fed. Rep. of Germany ....... 2830949

[51] Int. Cl.$^3$ .......................... C08J 9/10; C08J 9/12; C08J 9/14
[52] U.S. Cl. ................................ 521/107; 521/125; 521/902; 521/906; 528/51
[58] Field of Search .............. 521/107, 125, 902, 906; 528/51; 260/502.4

[56] References Cited

U.S. PATENT DOCUMENTS

| | | | |
|---|---|---|---|
| 3,899,443 | 8/1975 | Reymore, Jr. | 521/902 |
| 3,953,384 | 4/1976 | Fouratson | 521/902 |
| 4,075,139 | 2/1978 | Greer | 521/107 |

*Primary Examiner*—Morton Foelak
*Attorney, Agent, or Firm*—Gene Harsh; Joseph C. Gil

[57] ABSTRACT

The instant invention is directed to phosphonates of the formulae:

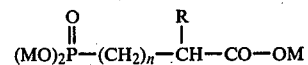

in which
n represents an integer of from 0 to 3,
R represents H or —(CH$_2$)$_m$—COOM,
m represents an integer of from 0 to 3,
M represents an alkali metal, or NR'$_4$ wherein R' represents H or a C$_1$–C$_4$ alkyl group;

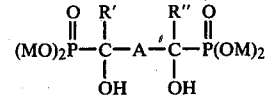

in which
A represents (CH$_2$)$_x$ or C$_6$–C$_{10}$ arylene (preferably phenylene),
x represents an integer of from 0 to 5,
R' and R" which may be the same or different represent H or a C$_1$–C$_4$ alkyl group, and
M represents an alkali metal, or NR'$_4$.

The invention is also directed to the use of these phosphonates as trimerization catalysts.

8 Claims, No Drawings

USE OF PHOSPHONATES AS TRIMERIZATION CATALYSTS FOR THE PRODUCTION OF POLYISOCYANURATE SYNTHETIC RESINS

BACKGROUND OF THE INVENTION

This invention relates to new phosphonates, and to their use as catalysts for the production of polyisocyanurate synthetic resins.

Numerous catalysts for the production of isocyanurate synthetic resins are known but the problem of the flow properties of foamable polyisocyanurate reaction mixtures has not previously been satisfactorily solved with these known catalysts. It has been found that the reaction mixture which gives rise to the polyisocyanurate form is in many cases insufficiently fluid so that when it is foamed in molds it frequently does not sufficiently fill the cavities and corners.

It has surprisingly been found that the flow of polyisocyanurate foams can be substantially improved by means of the catalysts of the instant invention.

DESCRIPTION OF THE INVENTION

This invention therefore relates to a process for the production of synthetic resins containing isocyanurate groups and optionally urethane groups, including foam resins of this type, by the trimerization of polyisocyanates with the aid of isocyanate trimerization catalysts, optionally in the presence of blowing agents, foam stabilizers and other additives, optionally in the presence of less than the equivalent quantity of polyhydroxyl compounds with a number average molecular weight of from 400 to 10,000 as determined by gel permeation chromatography which have at least two hydroxyl groups and optionally chain lengthening agents with a number average molecular weight of from 32 to 400 as determined by gel permeation chromatography, characterized in that as trimerization catalysts there are used phosphonates corresponding to the following general formula $$(MO)_2\overset{O}{\overset{\|}{P}}-(CH_2)_n-\overset{R}{\overset{|}{CH}}-CO-OM \quad (I)$$

in which n represents an integer of from 0 to 3,

R represents H or $-(CH_2)_m$-COOM, m represents an integer of from 0 to 3, and

M represents an alkali metal, preferably Na or K, or $NR'_4$ in which

R' represents H or a $C_1$-$C_4$ alkyl group, and/or phosphonates corresponding to the following general formula $$(MO)_2\overset{O}{\overset{\|}{P}}-\overset{R'}{\underset{OH}{\overset{|}{C}}}-A-\overset{R''}{\underset{OH}{\overset{|}{C}}}-\overset{O}{\overset{\|}{P}}(OM)_2 \quad (II)$$

in which

A represents $(CH_2)_x$ or $C_6$-$C_{10}$ arylene, preferably phenylene x represents an integer of from 0 to 5, R' and R" which may be the same or different represent H or a $C_1$-$C_4$ alkyl group and M represents an alkali metal, preferably Na or K, or $NR'_4$.

The invention also relates to phosphonates corresponding to the following general formula $$(MO)_2\overset{O}{\overset{\|}{P}}-(CH_2)_n-\overset{R}{\overset{|}{CH}}-CO-OM \quad (I)$$

in which n represents an integer of from 0 to 3,

R represents H or $(CH_2)_m$COOM, m represents an integer of from 0 to 3, and

M represents an alkali metal, preferably Na or K, or $NR'_4$ in which

R' represents H or a $C_1$-$C_4$ alkyl group, and phosphonates corresponding to the following general formula $$(MO)_2\overset{O}{\overset{\|}{P}}-\overset{R'}{\underset{OH}{\overset{|}{C}}}-A-\overset{R''}{\underset{OH}{\overset{|}{C}}}-\overset{O}{\overset{\|}{P}}(OM)_2 \quad (II)$$

in which

A represents $(CH_2)_x$ or $C_6$-$C_{10}$ arylene, preferably phenylene, x represents an integer of from 0 to 5, R' and R" which may be the same or different represent H or a $C_1$-$C_4$ alkyl group and M represents an alkali metal, preferably Na or K, or $NR'_4$.

Compounds I and II are prepared as follows:

The compounds corresponding to the general formula I may be obtained, for example, by the addition of dialkyl phosphites such as dimethyl phosphite, diethyl phosphite or dipropyl phosphite to $\alpha,\beta$-unsaturated carbonyl compounds, e.g. maleic acid-di-($C_1$-$C_4$-alkyl) esters, itaconic acid-di-($C_1$-$C_4$-alkyl)esters or acetyle acetone, and hydrolysis of the resulting phosphonic acid esters.

The addition of dialkyl phosphites, e.g. of the type mentioned above, to dicarbonyl compounds such as butane dione, pentane dione, hexane dione or 1,4-diformyl benzene is a smooth reaction resulting in the formation of bifunctional $\alpha$-hydroxy phosphonic acid esters which are converted by hydrolysis into compounds corresponding to the general formula II.

Hydrolysis may be carried out, for example, by heating the esters formed, e.g. with equivalent quantities of the corresponding alkali metal hydroxides or ammonium hydroxides, e.g. in methanolic solution. Compounds I and II are Li, Na, K, Rb or Cs salts, preferably Na or K salts, or ammonium salts.

The following are examples of the new compounds I and II:

$$\overset{MO}{\underset{MO}{\diagdown}}\overset{O}{\overset{\|}{P}}-(CH_2)_2-\overset{O}{\overset{\|}{C}}-OM$$

Preferred

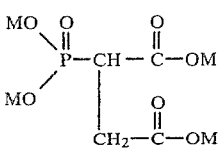

Preferred

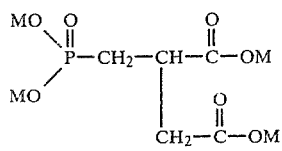

Preferred

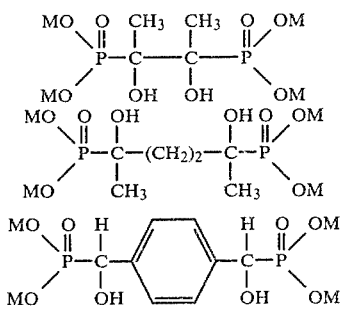

Preferred

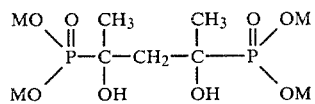

Preferred

M represents Na or K.

The compounds of the invention corresponding to the general formulae I and II are generally used in a quantity of from 0.01 to 20% by weight, preferably from 0.1 to 10% by weight, based on the polyisocyanates present. They are catalysts for the production of polyisocyanurate synthetic resins, preferably in the form of solutions in polyfunctional alcohols. The preferred alcohols are ethylene glycol, diethylene glycol, dipropylene glycol or tripropylene glycol.

The following are used for the production of synthetic resins containing isocyanurate groups:

1. The isocyanates may be aliphatic, cycloaliphatic, araliphatic, aromatic and heterocyclic polyisocyanates such as those described, for example, by W. Siefken by Justus Liebigs Annalen der Chemie, 562, pages 75 to 136. Examples include those corresponding to the following formula:

$$Q(NCO)_n$$

in which n=2 to 4, preferably 2, and

Q represents an aliphatic hydrocarbon group having from 2 to 18, preferably from 6 to 10 carbon atoms, a cycloaliphatic hydrocarbon group having from 4 to 15, preferably from 5 to 10 carbon atoms, an aromatic hydrocarbon group having from 6 to 15, preferably from 6 to 13 carbon atoms, or an araliphatic hydrocarbon group having from 8 to 15, preferably from 8 to 13 carbon atoms. Examples of possible isocyanates include: ethylene-diisocyanate; 1,4-tetramethylene diisocyanate; 1,6-hexamethylene diisocyanate; 1,12-dodecane diisocyanate; cyclobutane-1,3-diisocyanate; cyclohexane-1,3- and -1,4-diisocyanate and any mixtures of these isomers; 1-isocyanate-3,3,5-trimethyl-5-isocyanatomethyl-cyclohexane (German Auslegeschrift No. 1,202,785, and U.S. Pat. No. 3,401,190); hexahydrotolylene-2,4- and -2,6-diisocyanate and any mixture of these isomers; hexahydrophenylene-1,3- and/or 1,4-diisocyanate; perhydrodiphenyl methane-2,4'- and/or 4,4'-diisocyanate; phenylene-1,3- and -1,4-diisocyanate; tolylene-2,4- and -2,6-diisocyanate and any mixtures of these isomers; diphenyl methane-2,4'- and/or -4,4'-diisocyanate and naphthylene-1,5-diisocyanate.

The following, for example, may also be used in the invention: triphenylmethane-4,4',4''-triisocyanate; polyphenyl-polymethylene polyisocyanates which can be obtained by aniline formaldehyde condensation followed by phosgenation (British Pat. Nos. 874,430 and 848,671); m- and p-isocyanatophenyl-sulfonyl isocyanates (U.S. Pat. No. 3,454,606); perchlorinated aryl polyisocyanates (German Auslegeschrift No. 1,157,601 or U.S. Pat. No. 3,277,138); polyisocyanates having carbodiimide groups (German Pat. No. 1,092,007, U.S. Pat. No. 3,152,162 and German Offenlegungsschriften Nos. 2,504,400; 2,537,685 and 2,552,350); norbornan diisocyanates (U.S. Pat. No. 3,492,330); polyisocyanates with allophanate groups (British Pat. No. 994,890, Belgian Pat. No. 761,626 and Dutch Patent Application No. 7,102,524); polyisocyanates with isocyanurate groups (U.S. Pat. No. 3,001,973, German Pat. Nos. 1,022,789; 1,222,067 and 1,027,394 and German Offenlegungsschriften Nos. 1,929,034 and 2,004,048); polyisocyanates with urethane groups (Belgian Pat. No. 752,261 and U.S. Pat. Nos. 3,394,164 and 3,644,457); polyisocyanates with acylated urea groups (German Pat. 1,230,778); polyisocyanates with biuret groups (U.S. Pat. Nos. 3,124,605; 3,201,372 and 3,124,605 and British Pat. No. 889,050); polyisocyanates prepared by telomerization reactions (U.S. Pat. No. 3,654,106); polyisocyanates with ester groups (British Pat. Nos. 965,474 and 1,072,956, U.S. Pat. No. 3,567,763 and German Pat. No. 1,231,688); reaction products of the above-mentioned isocyanates with acetals (German Pat. No. 1,072,385) and polyisocyanates containing polymeric fatty acid groups (U.S. Pat. No. 3,455,883).

The distillation residues obtained from the commercial production of isocyanates and still containing isocyanate groups may also be used, optionally as solutions in one or more of the above-mentioned polyisocyanates. Any mixtures of the above-mentioned polyisocyanates may also be used.

It is particularly preferred to use readily available polyisocyanates such as tolylene-2,4-diisocyanate and -2,6-diisocyanate and any mixtures of these isomers ("TDI"); polyphenyl-polymethylene polyisocyanates of the kind which can be prepared by aniline-formaldehyde condensation followed by phosgenation ("crude MDI"); and polyisocyanates containing carbodiimide groups, urethane groups, allophanate groups, isocyanurate groups, urea groups or biuret groups ("modified polyisocyanates"), in particular those modified polyisocyanates which are derived from 2,4- and 2,6-tolylene diisocyanate or from 4,4'- and/or 2,4'-diphenylmethane diisocyanate.

2. The starting components used in the invention may also include compounds, generally with a number average molecular weight of 400 to 10,000 as determined by gel permeation chromatography, which have at least two isocyanate-reactive hydrogen atoms. These compounds may contain amino groups, thiol groups or carboxyl groups but are preferably hydroxyl group-containing compounds. These compounds preferably have from 2 to 8 hydroxyl groups, especially those with a molecular weight of from 1,000 to 5,000, preferably from 800 to 3,000, e.g. polyesters, polyethers, polythioethers, polyacetals, polycarbonates and polyester amides having at least 2, generally 2 to 8 but preferably 2 to 4 hydroxyl groups, of the kind known for the production of both homogeneous and cellular polyurethanes.

(a) Suitable polyesters with hydroxyl groups include e.g. reaction products of polyhydric and polybasic acids. The preferred polyhydric acids are dihydric alcohols, to which trihydric alcohols may be added. The polybasic acids are preferably dibasic, carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic. Also, they may be substituted, e.g. by halogen atoms, and/or unsaturated.

The following are mentioned as examples of such carboxylic acids and their derivatives: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimerized and trimerized unsaturated fatty acids (which may be mixed with monomeric unsaturated fatty acids, such as oleic acid), dimethyl terephthalate and terephthalic acid-bis-glycol esters.

The following are examples of suitable polyhydric alcohols: ethylene glycol, propylene glycol-(1,2) and -(1,3), butylene glycol-(1,4) and -(2,3), hexanediol-(1,6), octanediol-(1,8), neopentylglycol, 1,4-bis-hydroxymethyl cyclohexane, 2-methyl-1,3-propanediol glycerol, trimethylolpropane, hexanetriol-(1,2,6), butanetriol-(1,2,4), trimethylolethane, pentaerythritol, quinitol, mannitol and sorbitol, formitol, methylglycoside, diethylene glycol, triethylene glycol, tetraethylene glycol and higher polyethylene glycols, dipropylene glycol and higher polypropylene glycols, and dibutylene glycol and higher polybutylene glycols. The polyesters may also contain a proportion of carboxyl end groups. Polyesters of lactones such as ε-caprolactone or of hydroxycarboxylic acids such as ω-hydroxycaproic acid may also be used.

(b) The polyethers which may be used in the invention have at least 2, generally 2 to 8, preferably 2 to 3 hydroxyl groups. They may be prepared by polymerization of epoxides such as ethylene oxide, propylene oxide, butylene oxide, tetrahydrofuran, styrene oxide or epichlorohydrin. The epoxides may be prepared either each on its own, e.g. in the presence of Lewis catalysts such as boron trifluoride, or by the addition of these epoxides, either as mixtures or successively, to starting components having reactive hydrogen atoms. Possible reactive hydrogen components include water alcohols, ammonia or amines, e.g. ethylene glycol, propylene glycol-(1,3) or -(1,2), trimethylolpropane, glycerol, sorbitol, 4,4'-dihydroxydiphenylpropane, aniline, ethanolamine or ethylene diamine. Sucrose polyethers (German Ausleschriften Nos. 1,176,358 and 1,064,938) and polyethers started on formitol or formose (German Offenlegungsschriften Nos. 2,639,083 and 2,737,951) may also be in the invention. It is in many cases preferred to use polyethers which contain predominantly primary hydroxyl groups (up to 90% by weight, based on all the hydroxyl groups present in the polyether). Polybutadienes containing hydroxyl groups are also suitable.

(c) The possible polythioethers include the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the cocomponents.

(d) Suitable polyacetals include the compounds which can be prepared from glycols such as diethylene glycol, triethylene glycol, 4,4'-dioxethoxy-diphenyl dimethylmethane, hexanediol and formaldehyde. Polyacetals suitable for the purpose of the invention may also be prepared by the polymerization of cyclic acetals, e.g. of trioxane (German Offenlegungsschrift No. 1,694,128).

(e) The polycarbonates with hydroxyl groups used may be of the kind known per se, for example those which can be prepared by the reaction of diols, such as propanediol-(1,3), butanediol-(1,4) and/or hexanediol-(1,6), diethylene glycol, triethylene glycol or tetraethylene glycol or thiodiglycol, with diarylcarbonates, e.g. with diphenyl carbonate or phosgene (German Ausleschriften Nos. 1,694,080; 1,915,908; and 2,221,751 and German Offenlegungsschrift No. 2,605,024).

(f) Suitable polyester amides and polyamides include the predominantly linear condensates prepared from polyvalent saturated and unsaturated carboxylic acids or their anhydrides and polyvalent saturated and unsaturated amino alcohols, diamines, polyamines and mixtures thereof.

(g) Polyhydroxyl compounds already containing urethane or urea groups and modified or unmodified natural polyols such as castor oil or carbohydrates, e.g. starch, may also be used. Addition products of alkylene oxides and phenol formaldehyde resins or of alkylene oxides and urea formaldehyde resins are also suitable for the purpose of the invention.

(h) The polyhydroxyl compounds mentioned above may be modified in various ways before they are used in the polyisocyanate polyaddition process. A mixture of different polyhydroxyl compounds (e.g. of a polyether polyol and a polyester polyol) may be condensed by etherification in the presence of a strong acid to form a higher molecular polyol consisting of different segments linked by ether bridges (German Offenlegungsschriften Nos. 2,210,839 and 2,544,195 and U.S. Pat. No. 3,849,515). Amide groups may be introduced into the polyhydroxyl compounds (German Offenlegungsschrift No. 2,559,372). Triazine groups may be introduced by a reaction with polyfunctional cyanic acid esters (German Offenlegungsschrift No. 2,620,487). Polyhydroxyl compounds containing guanidine, phosphonoformamidine or acylurea groups may be obtained by the reaction of a polyol with a less than equivalent quantity of a diisocyanatocarbodiimide, followed by reaction of the carbodiimide group with an amine, amide, phosphite or carboxylic acid (German Offenlegungsschriften Nos. 2,714,289; 2,714,292 and 2,714,293). It is in some cases of particular interest to convert the higher molecular polyhydroxyl compounds completely or partly into the corresponding anthranilic acid esters by a reaction with isatoic acid anhydride (German Offenlegungsschriften Nos. 2,019,432 and 2,619,840 and U.S. Pat. Nos. 3,808,250; 3,975,428 and 4,016,143). Higher molecular compounds having aromatic amino end groups are obtained in this way. Higher molecular compounds with amino end groups may be obtained by the reaction of isocyanate prepolymers with hydroxyl group-containing enamines, aldimines or ketimines, followed by hydrolysis (German Offenlegungsschrift No. 2,546,536 and U.S. Pat. No. 3,865,791). Other methods of preparing higher molecular compounds having amino end groups or hydrazide end groups are described in German Offenlegungsschrift No. 1,694,152 (U.S. Pat. No. 3,625,871).

(i) According to the invention, polyhydroxyl compounds which contain high molecular polyadducts or polycondensates or polymers in a finely dispersed or dissolved form may also be used. Polyhydroxyl compounds of this type may be obtained by carrying out polyaddition reactions (e.g. reactions between polyisocyanates and amino functional compounds) or polycondensation reactions (e.g. between formaldehyde and phenols and/or amines) in situ in the above-mentioned hydroxyl compounds. Processes of this kind have been described in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833; 2,550,862; 2,633,293 and 2,639,254. Polyhydroxyl compounds of this type can also be obtained by mixing a previously prepared polymer dispersion with a polyhydroxyl compound and then removing the water from the mixture (U.S. Pat. No. 3,869,413 and German Offenlegungsschrift No. 2,550,860).

Polyhydroxyl compounds which are modified with vinyl polymers, e.g. the polyhydroxyl compounds obtained by the polymerization of styrene and acrylonitrile in the presence of polyethers (U.S. Pat. Nos. 3,383,351; 3,304,273; 3,523,093 and 3,110,695 or German Auslegeschrift No. 1,152,536) or polycarbonate polyols (German Pat. No. 1,769,795 or U.S. Pat. No. 3,637,909) are also suitable for the process according to the invention. When using polyether polyols which have been modified according to German Offenlegungsschriften Nos. 2,442,101; 2,644,922 and 2,646,141 by graft polymerization with vinyl phosphonic acid esters and optionally (meth)acrylonitrile, (meth)acrylamide or OH functional (meth)acrylic acid esters, synthetic resins with exceptionally high flame resistance are obtained. Polyhydroxyl compounds into which carboxyl groups have been introduced by radical graft polymerization with unsaturated carboxylic acids and optionally other olefinically unsaturated monomers (German Offenlegungsschriften Nos. 2,714,291; 2,739,620 and 2,654,746) are particularly advantageous for use in combination with mineral fillers.

When modified polyhydroxyl compounds of the type mentioned above are used as starting components in the polyisocyanate polyaddition process, they in many cases give rise to polyurethane synthetic resins which have substantially improved mechanical properties.

Representatives of these compounds which may be used according to the invention have been described in High Polymers, Volume XVI, "Polyurethanes, Chemistry and Technology", by Saunders and Frisch, Interscience Publishers, New York, London, Volume I, 1962, pages 32–42 and pages 44–54 and Volume II, 1964, pages 5–6 and 198–199 and in Kunststoff Handbuch, Volume VII, Vieweg Höchtlen, Carl Hanser Verlag, Munich, 1966, e.g. on pages 45–71.

Mixtures of the above-mentioned compounds which contain at least two isocyanate reactive hydrogen atoms and have a molecular weight of from 400 to 10,000 may also be used, for example mixtures of polyethers and polyesters.

It is particularly advantageous in some cases to use a combination of low melting and high melting polyhydroxyl compounds (German Offenlegungsschrift No. 2,706,297).

3. The starting components used according to the invention may also include compounds with a molecular weight of from 32 to 400 which have at least two isocyanate reactive hydrogen atoms. Compounds containing hydroxyl groups and/or amino groups and/or thiol groups and/or carboxyl groups, preferably hydroxyl groups and/or amino groups, may serve as chain lengthening agents or cross linking agents. They generally have from 2 to 8, preferably 2 to 4, isocyanate reactive hydrogen atoms.

These may also be used as mixtures with various compounds with a molecular weight of from 32 to 400 which have at least two isocyanate reactive hydrogen atoms. The following are examples of such compounds: ethylene glycol, propyleneglycol-(1,2) and -(1,3), butyleneglycol-(1,4) and -(2,3), pentanediol-(1,5), hexanediol-(1,6), octanediol-(1,8), neopentylglycol, 1,4-bis-hydroxymethyl-cyclohexane, 2-methyl-1,3-propanediol, dibromobutenediol (U.S. Pat. No. 3,723,392), glycerol, trimethylolpropane, hexanetriol-(1,2,6), trimethylolethane, pentaerythritol, quinitol, mannitol, and sorbitol, castor oil, diethylene glycol, triethylene glycol, tetramethylene glycol, higher polyethylene glycols with a molecular weight of up to 400, dipropylene glycol, higher polypropylene glycols with a molecular weight of up to 400, dibutylene glycol, higher polybutylene glycols with a molecular weight of up to 400, 4,4'-dihydroxy-diphenylpropane, dihydroxymethyl-hydroquinone, ethanolamine, diethanolamine, N-methyldiethanolamine, triethanolamine and 3-aminopropanol.

The low molecular weight polyols used according to the invention may also be mixtures of hydroxy aldehydes and hydroxy ketones ("formoses") and the polyhydric alcohols obtained from them by reduction ("formitol") such as are formed from the autocondensation of formaldehyde hydrate in the presence of metal compounds as catalysts and compounds capable of enediol formation as cocatalysts (German Offenlegungsschriften Nos. 2,639,084; 2,714,084; 2,714,104; 2,721,186; 2,738,154 and 2,738,512). To obtain synthetic resins with improved flame resistance, these formoses are advantageously used in combination with aminoplast formers and/or phosphites (German Offenlegungsschriften Nos. 2,738,513 and 2,738,532). Solutions of polyisocyanate polyaddition products, in particular of polyurethane ureas containing ionic groups and/or polyhydrazodicarbonamides in low molecular polyhydric alcohols may also be used as polyol components according to the invention (German Offenlegungsschrift No. 2,638,759).

The following are examples of aliphatic diamines which are suitable for the process according to the invention: ethylenediamine, 1,4-tetramethylenediamine, 1,11-undecamethylenediamine, 1,12-dodecamethylenediamine and mixtures thereof, 1-amino-3,3,5-trimethyl-5-amino-methyl cyclohexane ("isophorone diamine"), 2,4- and 2,6-hexahydrotolylene diamine and mixtures thereof, perhydro-2,4'- and -4,4'-diaminodiphenyl methane, p-xylylene diamine, bis-(3-aminopropyl)-methylamine, diamino-perhydroanthracene (German Offenlegungsschrift No. 2,638,731) aand cycloaliphatic triamines according to German Offenlegungsschrift No. 2,614,244. Hydrazine and substituted hydrazines such as methyl hydrazine and N,N'-dimethyl hydrazine and their homologues as well as acid dihydrazides may be used according to the invention. Examples include carbodihydrazide, oxalic acid dihydrazide, the dihydrazides of malonic acid, succinic acid, glutaric acid, adipic acid, β-methyl adipic acid, sebacic acid, hydracrylic acid and terephthalic acid. Semicarbazido-alkylene-hydrazides such as β-semicarboazidopropionic acid hydrazide (German Offenlegungsschrift No. 1,770,591), semicarbazidoalkylene-carbazic esters such as 2-semicarboazidoethylcarbazic ester (German Offenlegungsschrift No. 1,918,504) and aminosemicarbazide compounds such as β-aminoethyl-semicarbazido carbonate (German Offenlegungsschrift No. 1,902,931) may also be used. The amino groups may be partly or completely blocked by aldimine or ketimine groups to control their reactivity (U.S. Pat. No. 3,734,894 and German Offenlegungsschrift No. 2,637,115).

The following are examples of suitable aromatic diamines: bis-anthranilic acid esters (German Offenlegungsschriften Nos. 2,040,644 and 2,160,590); 3,5- and 2,4-diaminobenzoic acid esters (German Offenlegungsschrift No. 2,025,900); ester group-containing diamines (German Offenlegungsschriften Nos. 1,803,635; 2,040,650 and 2,160,589; U.S. Pat. Nos. 3,681,290 and 3,736,350); ether group-containing diamines (German Offenlegungsschriften Nos. 1,770,525 and 1,809,172 or U.S. Pat. Nos. 3,654,364 and 3,736,295); 2-halogen-1,3-phenylene diamines which may be substituted in the 5-position (German Offenlegungsschriften Nos. 2,001,772; 2,025,896 and 2,065,869); 3,3'-dichloro-4,4'-diaminodiphenyl methane, tolylene diamine; 4,4'-diaminodiphenyl methane; 4,4'-diaminodiphenyl-disulfides (German Offenlegungsschrift No. 2,404,976); diaminodiphenyldithioethers (German Offenlegungsschrift No. 2,509,404); aromatic diamines substituted with alkylthio groups (German Offenlegungsschrift No. 2,638,760); diaminobenzene phosphonic acid esters (German Offenlegungsschrift No. 2,459,491); aromatic diamines containing sulfonate or carboxylate groups (German Offenlegungsschrift No. 2,720,166); and high melting diamines (German Offenlegungsschrift No. 2,635,400). Aminoalkylthioanilines according to German Offenlegungsschrift No. 2,734,574 are examples of aliphatic-aromatic diamines.

Compounds such as 1-mercapto-3-aminopropane; substituted or unsubstituted amino acids such as glycine, alanine, valine, serine and lysine; and substituted or unsubstituted dicarboxylic acids such as succinic acid, adipic acid, phthalic acid, 4-hydroxyphthalic acid or 4-aminophthalic acid may also be used as chain lengthening agents according to the invention.

Compounds which are monofunctional in their reactions with isocyanates may also be used as so-called chain breakers in proportions of from 0.01 to 10% by weight, based on the polyurethane solids content. Monofunctional compounds of this type include e.g. monoamines such as butylamine and dibutylamine, octylamine, stearylamine, N-methyl-stearylamine, pyrrolidine, piperidine and cyclohexylamine; monohydric alcohols such as butanol, 2-ethyl-hexanol, octanol or dodecanol; various amyl alcohols, cyclohexanol and ethyleneglycol monoethylether.

4. Auxiliary agents and additives may optionally be present:

(a) Water and/or readily volatile inorganic or organic substances as blowing agents. Examples of suitable organic blowing agents include acetone, ethyl acetate, and halogenated alkanes such as methylene chloride, chloroform, ethylidene chloride, vinylidene chloride, monofluorotrichloromethane, chlorodifluoromethane, and dichlorodifluoromethane, and butane, hexane, heptane and diethyl ethers. Air, carbon dioxide and nitrous oxide may be used as inorganic blowing agents. The effect of a blowing agent may also be obtained by the addition of compounds which decompose at temperatures above room temperature to release gases, for example compounds releasing nitrogen, e.g. azo compounds such as azodicarbonamide or azoisobutteric acid nitrile. Other examples of blowing agents and details concerning the use of blowing agents may be found in Kunststoff Handbuch, Volume VII, published by Vieweg and Höchtlen, Carl Hanser Verlag, Munich 1966, e.g. on pages 108 and 109, 453 to 455 and 507 to 510.

(b) Additional catalysts of known type in quantities of up to 50% by weight based on the catalysts to be used according to the invention, for example: tertiary amines such as triethylamine, tributylamine, N-methylmorpholine, N-ethyl morpholine, N,N,N',N'-tetramethylethylene diamine; pentamethyldiethylene triamine and higher homologues (German Offenlegungsschriften Nos. 2,624,527 and 2,624,528); 1,4-diazabicyclo-(2,2,2)-octane; N-methyl-N'-dimethylaminoethyl piperazine; bis-(dimethylaminoalkyl)-piperazines (German Offenlegungsschrift No. 2,636,787); N,N-dimethylbenzylamine; N,N-dimethylcyclohexylamine; N,N-diethylbenzylamine; bis-(N,N-diethylaminoethyl)-adipate; N,N,N',N'-tetramethyl-1,3-butanediamine; N,N-dimethyl-β-phenylethylamine; 1,2-dimethylimidazole; 2-methylimidazole; monocyclic and bicyclic amidines (German Offenlegungsschrift No. 1,720,633); bis-(dialkylamino)alkyl-ethers (U.S. Pat. No. 3,330,782, German Auslegeschrift No. 1,030,558 and German Offenlegungsschriften No. 1,804,361 and 2,618,280); and tertiary amines containing amide groups, preferably formamide groups, (German Offenlegungsschriften No. 2,523,633 and 2,732,292). Known Mannich bases of secondary amines (such as dimethylamine), aldehydes (preferably formaldehyde), ketones (such as acetones, methylethyl ketone or cyclo hexanone), and phenols (such as phenol, nonylphenol or bisphenol) may also be used as catalysts.

The following are examples of tertiary amines with isocyanate reactive hydrogen atoms which may be used as catalysts: triethanolamine, triisopropanolamine, N-methyl-diethanolamine, N-ethyl-diethanolamine, N,N-dimethyl-ethanolamine. Their reaction products with alkylene oxides such as propylene oxide and/or ethylene oxide and secondary-tertiary amines (German Offenlegungsschrift No. 2,732,292) may also be used.

Silaamines with carbon-silicon bonds (German Pat. No. 1,229,290 or U.S. Pat. No. 3,620,984) may also be used as catalysts, e.g. 2,2,4-trimethyl-2-silamorpholine or 1,3-diethylaminomethyl-tetramethyldisiloxane.

Nitrogen-containing bases such as tetraalkyl ammonium hydroxides, alkali metal hydroxides such as sodium hydroxide, alkali metal phenolates such as sodium phenolate and alkali metal alcoholates such as sodium methylate may also be used as catalysts. Hexahydrotriazines may be used as catalysts (German Offenlegungsschrift No. 1,769,043).

The reaction between isocyanate groups and Zerewitinoff active hydrogen atoms is also powerfully accelerated by lactam and azalactams, an associate between the lactam and the compound having an acidic hydrogen being formed first. Such associates and their catalytic action have been described in German Offenlegungsschriften Nos. 2,062,288; 2,062,289; 2,117,576 (U.S. Pat. No. 3,758,444); 2,129,198; 2,330,175 and 2,330,211.

Organic metal compounds may also be used as catalysts according to the invention, in particular organic tin compounds. Apart from those which contain sulfur, such as di-n-octyl-tin-mercaptide (German Auslegeschrift No. 1,769,367 and U.S. Pat. No. 3,645,927), it is particularly preferred to use tin(II)salts of carboxylic acids, such as tin(II)acetate, tin(II) octoate, tin(II)ethylhexoate and tin(II)laurate; and tin(IV) compounds such as dibutyl tin oxide, dibutyl tin dichloride, dibutyl tin diacetate, dibutyl tin dilaurate, dibutyl tin maleate and dioctyl tin diacetate.

All the catalysts mentioned above may also be used as mixtures. It is particularly interesting to use combinations of organic metal compounds with amidines, aminopyridines or hydrazinopyridines (German Offenlegungsschriften No. 2,434,185; 2,601,082 and 2,603,834).

Other representatives of catalysts which may be used according to the invention and details about the activity of the catalysts may be found in Kunststoff Handbuch, Volume VII, published by Vieweg and Höchtlen, Carl Hanser Verlag, Munich 1966, e.g. on pages 96 to 102.

The catalysts are generally used in a quantity of about 0.001 to 10% by weight, based on the total quantity of compounds having at least two isocyanate reactive hydrogen atoms.

(c) Surface active additives such as emulsifiers and foam stabilizers. As emulsifiers there may be used, for example, the sodium salts of ricinoleic sulfonates or salts of fatty acids with amines, such as oleic acid diethylamine or stearic acid diethanolamine. Alkali metal and ammonium salts of sulfonic acids, such as dodecylbenzene sulfonic acid or dinaphthyl methane disulfonic acid, or of fatty acids such as ricinoleic acid or of polymeric fatty acids may also be included as surface active additives.

The foam stabilizers to be considered are mainly polyether siloxanes, especially those which are water soluble. These compounds generally consist of a copolymer of ethylene oxide and propylene oxide to which a polydimethyl siloxane group is attached. Foam stabilizers of this type have been described in U.S. Pat. No. 2,834,748; 2,917,480 and 3,629,308. It is in many cases particularly interesting to use polysiloxane-polyoxyalkylene-copolymers branched via allophanate groups (German Offenlegungsschrift No. 2,558,523).

(d) Reaction retarders, e.g. compounds which are acid in reaction such as hydrochloric acid or organic acid halides; known cell regulators such as paraffins or fatty alcohols or dimethyl polysiloxanes; pigments, dyes, known flame retarding agents, e.g. tris-chloroethyl phosphate, tricresyl phosphate or ammonium phosphate and polyphosphate; stabilizers against aging and weathering, plasticizers, fungistatic and bacteriostatic substances and fillers such as barium sulphate, kieselguhr, carbon black or whiting.

Other examples of surface active additives, foam stabilizers, cell regulators, reaction retarders, stabilizers, flame retarding substances, plasticizers, dyes, fillers and fungistatic and bacteriostatic substances which may also be used according to the invention and details about their use and mode of action may be found in Kunststoff Handbuch, Volume VII, published by Vieweg and Höchtlen, Carl Hanser Verlag, Munich 1966, e.g. on pages 103 to 113.

According to the invention, the components are reacted together by the known one-shot process, prepolymer process or semi-prepolymer process, often using mechanical devices such as those described in U.S. Pat. No. 2,764,565. Details concerning processing apparatus which may also be used according to the invention are given in Kunststoff Handbuch, Volume VII, published by Vieweg and Höchtlen, Carl Hanser Verlag, Munich 1966, e.g. on pages 121 to 205.

Production of the foams according to the invention may be carried out in closed molds. The reaction mixture is introduced into a mold which may be made of a metal (preferably aluminum) or a synthetic resin (preferably an epoxide resin). The reaction mixture foams up inside the mold to form the shaped product. The process of foaming in the mold may be carried out in such a manner that the shaped product has a cellular structure on its surface but it may also be carried out to produce a shaped product having a noncellular skin and a cellular core. Just a sufficient quantity of reaction mixture may be introduced into the mold to fill the mold with foam after the reaction or a larger quantity of reaction mixture than is necessary may be introduced to fill the interior of the mold with foam. The latter method is known as "over-charging" (U.S. Pat. Nos. 3,178,490 and 3,182,104).

Known so-called "external mold release agents" such as silicone oils are frequently used for foaming inside molds. So-called "internal mold release agents" may also be used, such as those disclosed in German Offenlegungsschriften Nos. 2,121,670 and 2,307,589, optionally in combination with external mold release agents.

Foams may, of course, also be produced by block foaming or by the known laminator process.

The products obtainable according to the invention may be used, for example, as insulating boards or for roof insulation.

EXAMPLES

EXAMPLE 1a

Potassium salt of hydroxycarbonyl-ethane-phosphonic acid

Preparation of β-methoxycarbonylethane-phosphonic acid dimethyl ester.

To a solution of 76 g (1 mol) acrylic acid methyl ester and 110 g (1 mol) dimethylphosphit are added dropwise 10 ml of a 30% sodium methylate solution, thereafter the exothermic reaction is completed. The reaction mixture is stirred for further 30 minutes at 100° C. and then freed from low volatile constituents; yield quantitative. (Lit.: A. N. Pudovik, Z. obsc. Chim. 22, 473 (1952), C.A. 47, 4837 (1953) by K. Sasse in Houben Weyl, Volume XII/1, 467)

238 g (1 mol) of β-methoxycarbonylethane-phosphonic acid dimethyl ester are introduced dropwise into 500 ml of methanol and 168 g (3 mol) of potassium hydroxide, heated under reflux for 20 hours and then concentrated by evaporation and dried.

Yield quantitative; colorless hygroscopic powder readily soluble in ethylene glycol and diethylene glycol.

EXAMPLE 1b

Sodium salt of hydroxycarbonyl-ethane-phosphonic acid 238 g (1 mol) of β-methoxycarbonyl-ethane-phosphonic acid dimethyl ester are introduced dropwise into 500 ml of methanol and 120 g (3 mol) of sodium hydroxide, heated under reflux for 20 hours, concentrated by evaporation and dried. Quantitative yield of a colorless, hygroscopic powder readily soluble in ethylene glycol and diethylene glycol.

EXAMPLE 2a

α,β-bis-(methoxycarbonyl)-ethane-phosphonic acid dimethyl ester 20 ml of 5% sodium methylate solution are added dropwise to 144 g (1 mol) of dimethyl maleate and 110 g of dimethyl phosphite until the exothermic reaction is completed. The reaction mixture is stirred for a further 30 minutes at 100° C. and then freed from low volatility constituents.

Yield quantitative:

Analysis for $C_8H_{15}O_7P$ (254): Calculated C 37.8%, H 5.9%, P 12.2%; Found C 37.7%, H 6.4%, P 12.0%.

EXAMPLE 2b

Potassium salt of α,β-bis-(hydroxycarbonyl)-ethane-phosphonic acid 254 g (1 mol) of α,β-bis-(methoxycarbonyl)-ethanephosphonic acid dimethyl ester are added dropwise to 600 ml of methanol and 224 g (4 mol) of potassium hydroxide, heated under reflux for 20 hours and concentrated by evaporation. Quantitative yield of a colorless, hygroscopic powder readily soluble in lower monohydric and polyhydric alcohols.

EXAMPLE 3a

β,γ-bis-(methoxycarbonyl)-propane-phosphonic acid dimethyl ester 8 ml of a 30% sodium methylate solution are added dropwise to 158 g (1 mol) of itaconic acid dimethyl ester and 110 g of dimethyl phosphite at 60° C. The exothermic reaction is by that time completed. The mixture is then stirred for one hour at 100° C. and concentrated by evaporation. Quantitative yield of a colorless liquid.

Analysis for $C_9H_{17}O_7P$ (268); Calculated C 40.3%, H 6.35%, P 11.6%; Found C 40.5%, H 6.5%, P 11.7%.

EXAMPLE 3b

Potassium salt of β,γ-bis-(hydroxycarbonyl)-propane phosphonic acid 268 g (1 mol) of β,γ-bis-(methoxycarbonyl)-propanephosphonic acid dimethyl ester are added dropwise to a solution of 224 g (4 mol) of potassium hydroxide in 600 ml of methanol and the mixture is heated under reflux for 20 hours, concentrated by evaporation and dried. Quantitative yield of a colorless, hygroscopic powder completely soluble in lower monohydric and polyhydric alcohols.

EXAMPLE 4a 2,4-dihydroxy-pentane-diphosphonic acid dimethyl ester-(2,4)

15 ml of a 30% sodium methylate solution are added dropwise to 100 g (1 mol) of acetyl acetone and 220 g (2 mol) of dimethyl phosphite. The exothermic reaction has then been completed. The mixture is stirred for a further 2 hours at 80° C. and concentrated by evaporation. Quantitative yield of a viscous liquid.

Analysis for $C_9H_{22}O_8P_2$ (220); Calculated C 33.7%, H 6.8%, P 19.4%; Found C 33.0%, H 6.3%, P 19.8%.

EXAMPLE 4b

Potassium salt of 2,4-dihydroxy-pentane-diphosphonic acid-(2,4)

220 g (1 mol) of 2,4-dihydroxy-pentane-diphosphonic acid dimethyl ester-(2,4) are introduced dropwise into a solution of 600 ml of methanol and 224 g (4 mol) of potassium hydroxide and the reaction mixture is heated under reflux for 20 hours, concentrated by evaporation and dried. Quantitative yield of a colorless, hygroscopic powder which is completely soluble in ethylene glycol and diethylene glycol.

EXAMPLE 5a 2,3-dihydroxybutane-diphosphonic acid dimethyl ester-(2,3)

50 ml of a 3% sodium methylate solution are introduced dropwise into 172 g (2 mol) of diacetyl and 440 g (4 mol) of dimethyl phosphite. The reaction mixture is kept at 80° C. for 1 hour after the exothermic reaction has died down and is then freed from low volatility constituents in a vacuum.

Yield 540 g, corresponding to 87% of the theoretical yield.

Analysis for $C_8H_{20}O_8P_2$ (306); Calculated C 31.4%, H 6.5%, P 20.9%; Found C 31.3%, H 6.2%, P 19.8%.

EXAMPLE 5b

Potassium salt of 2,3-dihydroxy butane-diphosphonic acid-(2,3)

153 g (0.5 mol) of 2,3-dihydroxy butane-diphosphonic acid-dimethyl-ester-(2,3) are heated under reflux in 100 ml of methanol and 112 g (2 mol) of potassium hydroxide for 20 hours. The reaction mixture is then concentrated by evaporation and dried. Quantitative yield, readily soluble in lower monohydric and polyhydric alcohols.

EXAMPLE 6a 1,4-phenylene-bis-(hydroxymethane-phosphonic acid dimethyl ester)

20 ml of a 3% sodium methylate solution are added dropwise at about 80° C. to 110 g (1 mol) of dimethyl phosphite, 67 g (0.5 mol) of terephthalic aldehyde and 200 ml of dimethyl formamide. The reaction mixture is left at 80° C. for 1 hour after the exothermic reaction has died down and is then cooled, suction filtered and dried. Yield 145 g, corresponding to 82% of the theoretical yield; melting point 200° C.

Analysis for $C_{12}H_{20}O_8P_2$ (354); Calculated C 40.7%, H 5.65%, P 17.5%; Found C 40.0%, H 6.1%, P 16.9%.

EXAMPLE 6b

Potassium salt of
1,4-phenylene-bis-(hydroxymethyl-phosphonic acid)

177 g (0.5 mol) of 1,4-phenylene-bis-(hydroxymethane-phosphonic acid dimethyl ester) in 500 ml of methanol and 112 g (2 mol) of potassium hydroxide are heated under reflux for 20 hours, concentrated by evaporation and dried. Quantitative yield, readily soluble in lower monohydric and polyhydric alcohols.

EXAMPLE 7

A polyol mixture is prepared from 17 parts by weight of a sugar polyether having a hydroxyl number of 380 and a functionality of 4.7 obtained by the addition of propylene oxide to a mixture of sugar and water, 4 parts by weight of a polyether with a hydroxyl number of 650 constituting an adduct of propylene oxide and ethylene diamine, 10 parts by weight of a polyether with a hydroxyl number of 200 and a functionality of 3 obtained by the condensation of adipic acid, propylene glycol and glycerol, 1 part by weight of a commercial silicone stabilizer (L 5340 of Union Carbide Co.), and 14 parts by weight of trichloroethyl phosphate.

A preliminary mixture is first prepared from 45 parts by weight of this mixture, 25 parts by weight of trichlorofluoromethane and 2.5 parts by weight of the catalyst from Example 1b. This preliminary mixture and 100 parts by weight of a crude diphenyl methane diisocyanate prepared by aniline-formaldehyde condensation followed by phosgenation and having an isocyanate content of 31% are then mixed in a spray mixer of the type HK 100 Maschinenfabrik Henneke, Burlinghoven, and applied to the paper of a laminator system. Laminator boards are produced in known manner. The rise time is 10 seconds, the gel time 30 seconds and the gross density of the finished foam 35 kg/m³. The boards may be used for roof insulation. The foam is homogeneous and shows no uneveness of color.

EXAMPLE 8 (Comparison Example)

The procedure is the same as in Example 7 but the 2.5 parts by weight of catalyst according to Example 1b are replaced by 2 parts by weight of a 30% potassium acetate solution in diethylene glycol.

The foaming mixture has a rise time of 14 seconds and a gel time of 29 seconds. Its expansion and foaming characteristics are markedly inferior. The foam has pronounced color shadings in the finished boards and numerous cavities, due to uneven expansion and foaming, under the upper surface layer.

EXAMPLE 9

The procedure is the same as in Example 7 but 0.5 parts by weight of the catalyst from Example 1b are replaced by 0.2 parts by weight of dimethyl cyclohexylamine. The catalyst to be used according to the invention is thus partly replaced by a known catalyst.

The rise time is 9 seconds and the gel time 30 seconds and the properties of the foam panels are similar to those of Example 7.

EXAMPLE 10

A preliminary mixture is prepared from 40 parts by weight of the polyol mixture from Example 7, 20 parts by weight of trichlorofluoromethane and 3 parts by weight of the catalyst from Example 2b. This preliminary mixture is vigorously mixed for 20 seconds with 100 parts by weight of a prepolymer prepared from 95% by weight of the isocyanate from Example 7 and 5% by weight of tetrapropylene glycol (isocyanate content of the prepolymer: 28%).

The rise time is 60 seconds, the gel time 140 seconds. The foam obtained has a gross density of 35 kg/m³ and is graded B2 in the flame proof classification according to DIN 4102.

The foam can be further processed, e.g. for the manufacture of insulation boards and half shells for pipes.

EXAMPLE 11

A polyol mixture is prepared from 10 parts by weight of a polyether with hydroxyl number 500 obtained by the addition of propylene oxide to sorbitol, 10 parts by weight of a polyether with hydroxyl number 56 constituting an adduct of propylene oxide and propylene glycol, 10 parts by weight of diphenyl cresyl phosphate, 0.2 parts by weight of water and 0.2 parts by weight of the silicone stabilizer from Example 7.

This mixture is vigorously mixed by stirring with 100 parts by weight of the isocyanate from Example 7 and 8 parts by weight of the catalyst from Example 1b.

The rise time is 80 seconds, the gel time 240 seconds. The foam obtained has a gross density of 150 kg/m³ and may be used, for example, in the form of cut boards for floor insulation in deep freeze ware houses.

EXAMPLE 12

The procedure is the same as in Example 10 but the catalyst used there is replaced by 2 parts by weight of the catalyst from Example 3b.

The rise time is 60 seconds, the gel time 125 seconds. The foam is similar to that of Example 10.

EXAMPLE 13

The procedure is the same as in Example 10 but the catalyst used there is replaced by the catalyst according to Example 4b. The rise time is 100 seconds, the gel time 300 seconds. The foam is homogeneous and shows no color shadings.

What is claimed is:

1. In a process for the production of synthetic resins containing isocyanurate groups and optionally urethane groups, including foam resins, comprising trimerizing polyisocyanates using isocyanate trimerization catalysts, optionally in the presence of blowing agents, foam stabilizers and other additives, and optionally in the presence of a less than equivalent quantity of polyhydroxyl compounds with molecular weights of from 400 to 10,000 which have at least two hydroxyl groups and optionally chain lengthening agents with a molecular weight of from 32 to 400, the improvement wherein said trimerization catalysts are phosphonates corresponding to the formula:

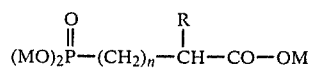

in which
   n represents an integer of from 0 to 3,
   R represents H or —(CH$_2$)$_m$—COOM,
   m represents an integer of from 0 to 3,
   M represents an alkali metal, or NR'$_4$ wherein R' represents H or a C$_1$-C$_4$ alkyl group.

2. The process of claim 1, wherein M represents sodium or potassium.

3. The process of claim 1, wherein 0.01 to 20%, by weight, based on the polyisocyanate present, of said trimerization catalyst is used.

4. The process of claim 3, wherein 0.1 to 10% is used.

5. The process of claim 1, wherein said trimerization catalyst is used in the form of a solution in polyfunctional alcohol.

6. The process of claim 5, wherein said alcohol is selected from the group consisting of ethylene glycol, diethylene glycol, dipropylene glycol and tripropylene glycol.

7. The process of claim 2, wherein n is 1 and R is hydrogen.

8. The process of claim 2, wherein n is 2 and R is $CH_2$—COOM.

* * * * *